United States Patent [19]

Baldwin et al.

[11] 3,984,558

[45] Oct. 5, 1976

[54] 1,3,5-TRISUBSTITUTED-1,2,4-TRIAZOLE COMPOUNDS USED AS BRONCHODILATORS

[75] Inventors: John J. Baldwin, Lansdale; Frederick C. Novello, Berwyn, both of Pa.

[73] Assignee: Merck & Co., Inc., Rahway, N.J.

[22] Filed: Nov. 29, 1974

[21] Appl. No.: 527,994

Related U.S. Application Data

[62] Division of Ser. No. 361,914, May 21, 1973, Pat. No. 3,882,134.

[52] U.S. Cl. .............................. 424/263; 424/248
[51] Int. Cl.² .......................................... A61K 31/44
[58] Field of Search ................. 424/263; 260/296 R

[56] References Cited

UNITED STATES PATENTS

| | | | |
|---|---|---|---|
| 3,308,131 | 3/1967 | McKusick | 260/293.69 |
| 3,882,134 | 5/1975 | Baldwin et al. | 260/296 R |

*Primary Examiner*—Leonard Schenkman
*Attorney, Agent, or Firm*—Daniel T. Szura; J. J. Behan

[57] ABSTRACT

Compounds useful in the treatment of asthma, the symptoms of allergy and in some instances in gout and hyperuricemia are described. The novel compounds are 1-substituted-1,2,4-triazoles being additionally substituted at the 3- and 5-positions with a pyridyl radical. Methods of preparing these tri-substituted triazoles are described.

12 Claims, No Drawings

1,3,5-TRISUBSTITUTED-1,2,4-TRIAZOLE COMPOUNDS USED AS BRONCHODILATORS

FIELD OF THE INVENTION

This is a division of application Ser. No. 361,914 filed May 21, 1973, now U.S. Pat. No. 3,882,134 issued May 6, 1975.

The invention relates to certain 1,2,4-triazoles trisubstituted in the 1, 3 and 5 positions, which are principally useful in the alleviation of symptoms of asthma and allergy as well as, in some instances, in the treatment of gout and as anti-hyperuricemic agents.

The trisubstituted-1,2,4-triazole compounds of this invention have been found in animal studies to inhibit bronchial constriction induced by histamine and other constricting agents and are therefoe useful as bronchodilating agents in the treatment of asthma and allergy. As bronchodilating agents, the products of this invention have been found to have relatively low chronotropic effect as compared with known bronchial dilator agents. Additionally, some of the products possess useful xanthine oxidase inhibiting properties, and are therefore useful in the treatment of gout and as anti-hyperuricemic agents, and some exhibit antihypertensive properties.

SUMMARY OF THE INVENTION

The novel compounds of this invention have the structure represented by Formulas I and Ia

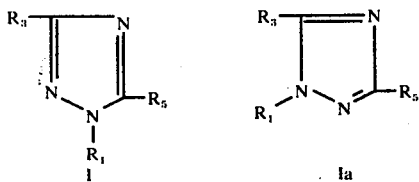

wherein $R_1$ represents a substituted lower alkyl ($C_{1-5}$) wherein the substituent is selected from one or more of the groups hydroxy, phenyl, halophenyl (especially chlorophenyl), nitrophenyl, sulfamoylphenyl (especially N,N-di($C_{1-5}$-alkyl)sulfamoylphenyl), tertiary amino (especially di-$C_{1-3}$-alkylamino, piperidino, morpholino, pyridyl [2, 3 or 4]) carboxy, and cyano; and $R_3$ and $R_5$ may be the same or different and separately represent 2, 3 or 4-pyridyl. Also useful for the same purpose are the pharmaceutically acceptable nontoxic acid salts of such compounds, the salts being of the pyridine ring present in the molecule.

The preferred compounds of this invention are those of Formulas I and Ia above wherein $R_1$ is phenalkyl or substituted phenalkyl where the substituent preferably is N,N-dialkylsulfamoyl and the alkyl moiety contains 1 carbon atom and $R_3$ and $R_5$ separately represent 4-pyridyl.

Included within the scope of the invention are the pharmaceutically acceptable acid addition salts, examples being the hydrochlorides, sulfates, tartrates, oxalates and the like.

The compounds of Formulas I and Ia can be prepared by reacting the desired preformed 3,5-di-pyridyl-triazole with an appropriate alkylating agent. Where $R_3$ and $R_5$ are dissimilar substituents, a mixture of compounds is obtained, i.e., the $R_1$ substituent may be substituted on either one of the adjacent nitrogens in the triazole ring. Alkylation is achieved by reacting the sodium salt of the triazole with an alkylating agent such as, for example, a substituted alkyl halide having the formula $R_1$-halide preferably the chloride, bromide or iodide.

The following examples are given for the purpose of illustration and not by way of limitation.

EXAMPLE 1

1-(2-Cyanoethyl)-3,5-bis(4-pyridyl)-1,2,4-triazole

Acrylonitrile (1 g.) is added to 3,5-bis(4-pyridyl)-1,2,4-triazole (1.1 g.) in pyridine (5 ml.). Five drops of triton B (N-benzyltrimethyl ammonium hydroxide) is added and the mixture heated at reflux for 2.5 hours. The solution is concentrated and the resulting solid is recrystallized from acetonitrile to yield 375 mg. of 1-(2-cyanoethyl)-3,5-bis(4-pyridyl)-1,2,4-triazole melting at 160°–161.5°C.

EXAMPLE 2

1-(2-Cyanoethyl)-3,5-bis(3-pyridyl)-1,2,4-triazole

When 3,5-bis(3-pyridyl)-1,2,4-triazole is used in the process of Example 1 in place of 3,5-bis(4-pyridyl)-1,2,4-triazole, 1-(2-cyanoethyl)-3,5-bis(3-pyridyl)-1,2,4-triazole is obtained melting at 145°–147°C.

EXAMPLE 3

1-(2-Carboxyethyl)-3,5-bis(4-pyridyl)-1,2,4-triazole 1-(2-Cyanoethyl)-3,5-bis(4-pyridyl)-1,2,4-triazole (1 g.) is dissolved in concentrated hydrochloric acid (10 ml.) and the resulting solution is heated 4 hours on a steam bath. The reaction mixture is concentrated to a solid which is dissolved in water and the solution neutralized with aqueous ammonia. A solid separates and is recrystallized from acetonitrile-water yielding 0.6 g. of 1-(2-carboxyethyl)-3,5-bis(4-pyridyl)-1,2,4-triazole melting at 245°–246.5°C.

EXAMPLE 4

1-Benzyl-3,5-bis(4-pyridyl)-1,2,4-triazole

To 3,5-bis(4-pyridyl)-1,2,4-triazole (4.4 g., 0.02 mol) in dry tetrahydrofuran (200 ml.) is added 57% sodium hydride in mineral oil (1 g., 0.024 mol.) and the mixture is heated 45 minutes at reflux. The suspension is concentrated to a solid, N,N-dimethylformamide (70 ml.) and benzyl chloride (2.8 g., 0.022 mol.) are added. The mixture is stirred 0.5 hour at ambient temperature followed by 4 hours at steam bath temperature. The solution is concentrated to a gum, water is added and the material solidifies. After recrystallization from methylcyclohexane 1.4 g. of 1-benzyl-3,5-bis(4-pyridyl)-1,2,4-triazole, melting at 136°–138°C. is obtained.

EXAMPLES 5–17

Following substantially the same procedure described in Example 4, but replacing the benzyl chloride by an equivalent quantity of the alkylating agent identified in column 2 of the following table, the 1-$R_1$-3,5-bis(4-pyridyl)-1,2,4-triazole compound having the $R_1$ substituent identified in column 3 is obtained.

| Example No. | Alkylating Agent | $R_1$ | m.p. °C. |
| --- | --- | --- | --- |
| 5 | Br—CH₂—⟨O⟩—SO₂N(C₃H₇)₂ | —CH₂—⟨O⟩—SO₂N(C₃H₇)₂ | 103–106 |
| 6 | Cl—CH₂—⟨O⟩—NO₂ | —CH₂—⟨O⟩—NO₂ | 191–192 |
| 7 | Br—CH₂—⟨O⟩—Cl | —CH₂—⟨O⟩—Cl | 131–132 |
| 8 | Cl—CH₂—⟨pyridyl-O⟩ | —CH₂—⟨pyridyl-O⟩ | 160–161 |
| 9 | Cl—CH₂—⟨O,N⟩ | —CH₂—⟨O,N⟩ | 193–194 |
| 10 | Cl—CH₂—CH(OH)—CH₂OH | —CH₂—CH(OH)—CH₂OH | 178–180 |
| 11 | Cl—CH₂—⟨O⟩—Cl | —CH₂—⟨O⟩—Cl | 165–166.5 |
| 12 | Br—CH₂CH₂—CH₂OH | —CH₂—CH₂—CH₂—OH | 123–126 |
| 13 | BrCH₂CH₂—OH | —CH₂—CH₂—OH | 209.5–210.5 |
| 14 | Cl—CH₂—CH₂—N⟨morpholino⟩O | —CH₂—CH₂—N⟨morpholino⟩O | 121–123 |
| 15 | ClCH₂CH₂N(C₂H₅)₂ | —CH₂CH₂N(C₂H₅)₂ | 93–94.5 |
| 16 | ClCH₂—CH₂—NH⟨piperidyl⟩ | —CH₂—CH₂—NH⟨piperidyl⟩ | 75–76.5 |
| 17 | BrCH₂CH₂—⟨O⟩ | —CH₂CH₂—⟨O⟩ | 116 |

The invention further provides pharmaceutical compositions comprising, as active bronchodilating agent, at least one of the compounds according to the invention in association with a pharmaceutical carrier or excipient to which other active ingredients can be added, if desired. The product or products can be presented in a form suitable for administration orally (such as capsules, tablets or liquid preparations), or for parenteral administration (in the form of solutions or suspensions) or in aerosols prepared by conventional methods. For example, a capsule can be prepared by conventional methods employing lactose as an excipient and containing per unit dosage 10–25 mgs. of active compound. Unit dosages can range between about 5 to 100 mg. for administration as prescribed by the physician.

While this invention has been illustrated by certain specific members of the novel 1,3,5-trisubstituted-1,2,4-triazole products made by certain specific methods and formulated into certain specific dosage forms, it is to be understood that the invention is not to be considered limited by or to the specific embodiments illustrated but is to encompass other members of the novel products falling within the scope of the generic disclosure and claims as well as other methods or modifications of the methods described for their preparation and other formulations, all of which would be obvious in view of the teaching herein to one skilled in the art.

What is claimed is:

1. A pharmaceutical composition comprising a bronchodilating amount of a triazole of the formula

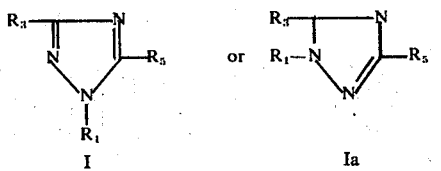

I     Ia or a pharmaceutically acceptable acid addition salt thereof, wherein $R_1$ is a substituted loweralkyl having from 1 to 2 of the substituents hydroxy, phenyl and chlorophenyl; $R_3$ is pyridyl and $R_5$ is pyridyl, and a pharmaceutically acceptable carrier.

2. A composition of claim 1 wherein $R_3$ and $R_5$ each represent 4-pyridyl.

3. A composition of claim 2 wherein $R_1$ is benzyl.

4. A composition of claim 2 wherein $R_1$ is

5. A composition of claim 2 wherein $R_1$ is —$CH_2$—CHOH—$CH_2OH$.

6. A composition of claim 2 wherein $R_1$ is

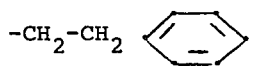

7. A composition of claim 2 wherein $R_1$ is selected from the group consisting of

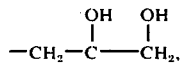

—$CH_2$—$CH_2$—$CH_2$—OH, and

—$CH_2$—$CH_2$—OH.

8. A composition of claim 2 wherein $R_1$ is —$CH_2$—$CH_2$—OH.

9. A composition of claim 2 wherein $R_1$ is —$CH_2$—$CH_2$—$CH_2$—OH.

10. A method for effecting bronchodilation comprising the administration to a host of an effective amount of a triazole of the formula

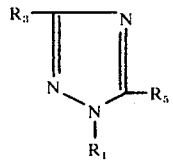 or 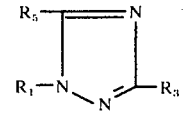

or pharmaceutically acceptable salts thereof, wherein
 $R_1$ is a substituted loweralkyl having from 1 to 2 of the substituents hydroxy, phenyl and chlorophenyl;
 $R_3$ is pyridyl and
 $R_5$ is pyridyl.

11. The method of claim 10 wherein said $R_1$ substituents are hydroxy, phenyl or chlorophenyl.

12. The method of claim 10 wherein $R_1$ is benzyl and $R_3$ and $R_5$ each represent 4-pyridyl.

* * * * *